US008177199B1

(12) United States Patent
Carpin

(10) Patent No.: US 8,177,199 B1
(45) Date of Patent: May 15, 2012

(54) AEROSOL GENERATOR

(75) Inventor: John C. Carpin, Perry Hall, MD (US)

(73) Assignee: The United States of America, as represented by the Secretary of the Army, Washington, DC (US)

( * ) Notice: Subject to any disclaimer, the term of this patent is extended or adjusted under 35 U.S.C. 154(b) by 470 days.

(21) Appl. No.: 12/570,006

(22) Filed: Sep. 30, 2009

Related U.S. Application Data

(60) Provisional application No. 61/118,115, filed on Nov. 26, 2008.

(51) Int. Cl.
*B01F 3/04* (2006.01)

(52) U.S. Cl. ............ 261/142; 261/78.2; 516/7; 516/922

(58) Field of Classification Search .................. 261/142, 261/78.2; 516/6, 7, 922
See application file for complete search history.

(56) References Cited

U.S. PATENT DOCUMENTS 5,160,664 A * 11/1992 Liu ................................... 516/7

* cited by examiner

*Primary Examiner* — Robert A Hopkins
(74) *Attorney, Agent, or Firm* — Ulysses John Biffoni

(57) ABSTRACT

An aerosol generator includes a saturator having an enclosure for passing a gas therethrough, and a porous substrate being adapted for retaining a non-vaporized form of an aerosol material, wherein the porous substrate is further adapted to release a vaporized form of the aerosol material for introduction into the gas within the enclosure, and a condenser adapted for receiving the gas containing the vapor from the saturator to produce an aerosol containing the aerosol material.

20 Claims, 3 Drawing Sheets

AEROSOL GENERATOR

RELATED APPLICATION

The present Application claims the benefit of priority from U.S. Provisional Patent Application Ser. No. 61/118,115, filed Nov. 26, 2008, the content of which is incorporated herein by reference to the extent it does not conflict herewith.

GOVERNMENT INTEREST

The invention described herein may be manufactured, used and licensed by or for the U.S. Government.

FIELD OF THE INVENTION

The present invention relates to aerosol generators, and more particularly to a highly efficient aerosol generator adapted for producing a highly concentrated monodisperse aerosol over an extended period of time from a relatively small volume of an aerosol material.

BACKGROUND OF THE INVENTION

Aerosols can be produced through a process of controlled condensation or vaporization-condensation. Generally such a process involves vaporizing an aerosol material and saturating a carrier gas with the generated vapor. The carrier gas and vapor is then cooled under laminar flow conditions. The controlled cooling initiates condensation of the vapor to yield an aerosol. To improve monodispersity and concentration of the aerosol, a common technique called heterogeneous condensation (HC) can be used. The HC technique involves the use of condensation nuclei or seed particles to assist in the formation of the aerosol particles to produce highly concentrated monodisperse aerosols from various liquid and solid aerosol materials.

Typically, a low volatility material (LVM) is selected for use as the aerosol material. The LVM is heated to produce a saturated vapor in the presence of a carrier gas and non-volatile condensation nuclei or seed particles (particle sizes of less than 0.1 $\mu M$) under low flow conditions. The condensation nuclei provide the surface needed to initiate particle formation and growth.

The mixture of vapor and condensation nuclei is thereafter cooled in a controlled manner under laminar flow conditions. The resulting supersaturation causes the vapor to uniformly condense onto the condensation nuclei, thereby yielding a monodisperse aerosol with particles having a narrow size distribution. The resulting particle sizes can be varied over a wide range of from about 0.5 $\mu m$ to 5.0 $\mu m$ by adjusting the ratio of vapor mass concentration to the number of condensation nuclei.

There are several aerosol generators commercially available on the market, which utilize HC to produce aerosols. Such aerosol generators are used for a variety of applications including observing the behavior of aerosols of specific particle sizes in a particular environment, effects of aerosols on electronic equipment, for example, and the toxicological effects of chemicals when inhaled. However, up to now, the use of such aerosol generators for highly toxic chemical agent testing has been very limited.

Aside from agent specific issues such as potential thermal breakdown and chemical reactivity, one of the principle factors limiting the use of HC aerosol generators is the relatively large quantity of agent needed for operation and the corresponding safety concerns for working personnel. Current aerosol generators commercially available in the market typically require a relatively large loading volume of the aerosol material, normally at least 100 ml, to produce a practical aerosol sample. Such aerosol generators generally include a saturator where the vapor of the aerosol material is produced to saturate the carrier gas passing therethrough. The saturator typically includes a boiler for holding the aerosol material and a heating element operatively associated with the boiler to heat the aerosol material to the state of vaporization. The carrier gas is then bubbled through the heated aerosol material, whereby the released vapor saturates the carrier gas.

The saturators are inherently inefficient, and therefore, require a sizable amount of aerosol material to produce an aerosol over a given period of time. Aerosol generators utilizing such saturators are especially impractical where the aerosol material is toxic and minimal handling is desired or where the aerosol material is expensive or in short supply. Such aerosol generators can pose undue safety hazards to the operators particularly where the aerosol material is highly toxic or dangerous to handle.

Accordingly, there is a need to develop an aerosol generator designed to produce highly concentrated monodisperse aerosols from an aerosol material with enhanced efficiency and reduced loading volumes of the aerosol material. There is a further need for an aerosol generator capable of producing highly concentrated monodisperse aerosols over an extended period of time from a relatively small volume of an aerosol material. There is a further need for a compact and lightweight aerosol generator for providing improved portability and convenient operation in a containment system such as, for example, a glove box.

SUMMARY OF THE INVENTION

The present invention relates generally to an aerosol generator adapted for producing a highly concentrated monodisperse aerosol composed of micron- and submicron-size particles from an aerosol material over an extended period of time, and from a relatively small volume of an aerosol material. The aerosol generator of the present invention utilizes a controlled condensation technique to produce the monodisperse aerosol. In particular, the aerosol generator of the present invention utilizes a vaporization-condensation process including, for example, heterogeneous condensation (HC). The technique involves vaporizing an aerosol material or a low volatility material, and allowing it to condense onto non-volatile seed particles or condensation nuclei. This results in the formation of an aerosol with a narrow size distribution. The aerosol generator can be used to produce monodisperse aerosols from a variety of low volatility liquid and solid materials. The aerosol generator of the present invention has the potential to produce near monodisperse aerosols over a wide range of sizes (0.3 to 5 micrometers)

Generally, the aerosol generator of the present invention includes a saturator for forming a vapor from a low volatility material or aerosol material, and a condenser for cooling the vapor of the aerosol material to produce the monodisperse aerosol. In the present invention, a high vaporization rate is achieved with small volumes of the aerosol material through the use of a custom designed saturator. Thus far, this has been proven to be a highly efficient approach for producing aerosols in the 0.7 to 5 micrometer size range with high output mass concentrations. Stable operation can be achieved for extended periods of time such as, for example, sixty minutes with loading volumes as low as 200 $\mu L$. The present invention provides a suitable applicability for testing of chemical agents when it is desirable to maintain quantities of test materials at a minimum.

The saturator of the present invention is designed to substantially enhance the efficiency and effective use of the aerosol material, thereby greatly reducing the loading volumes of the aerosol material and avoiding the limitations associated with prior art devices. Optionally, the aerosol generator of the present invention can further include a source of non-volatile sub-micron condensation nuclei, whereby the condenser cools the vapor of the aerosol material in the presence of the non-volatile sub-micron condensation nuclei to produce the monodisperse aerosol. The aerosol generator of the present invention is cost effective and relatively simple to make and implement.

In one aspect of the present invention, there is provided an aerosol generator, comprising:
a saturator including:
an enclosure for passing a gas therethrough; and
a porous substrate being adapted for retaining a non-vaporized form of an aerosol material, wherein the porous substrate is further adapted to release a vaporized form of the aerosol material for introduction into the gas within the enclosure; and
a condenser adapted for receiving the gas containing the vapor from the saturator to produce an aerosol containing the aerosol material.

In a further aspect of the present invention, there is provided an aerosol generator, comprising:
a condensation nuclei source for supplying condensation nuclei to a gas;
a saturator including:
an enclosure for passing the gas containing the condensation nuclei therethrough from the condensation nuclei source; and
a porous substrate being adapted for retaining a non-vaporized form of an aerosol material, wherein the porous substrate is further adapted to release a vaporized form of the aerosol material for introduction into the gas containing the condensation nuclei within the enclosure; and
a condenser adapted for receiving the gas containing the vapor and condensation nuclei from the saturator, wherein the vapor of the aerosol material condenses onto the condensation nuclei within the condenser to produce an aerosol containing the aerosol material.

In another aspect of the present invention, there is provided a saturator for an aerosol generator, comprising:
an enclosure for passing a gas containing condensation nuclei therethrough from a condensation nuclei source; and
a porous substrate being adapted for retaining a non-vaporized form of an aerosol material, wherein the porous substrate is further adapted to release a vaporized form of the aerosol material resulting in the formation of a vapor for introduction into the gas passing through the enclosure.

BRIEF DESCRIPTION OF THE DRAWINGS

The following drawings are illustrative of preferred embodiments of the present invention, and are not intended to limit the invention as encompassed by the claims forming part of the application, wherein like items are identified by the same reference designations:

DETAILED DESCRIPTION OF THE INVENTION

Figure 1:
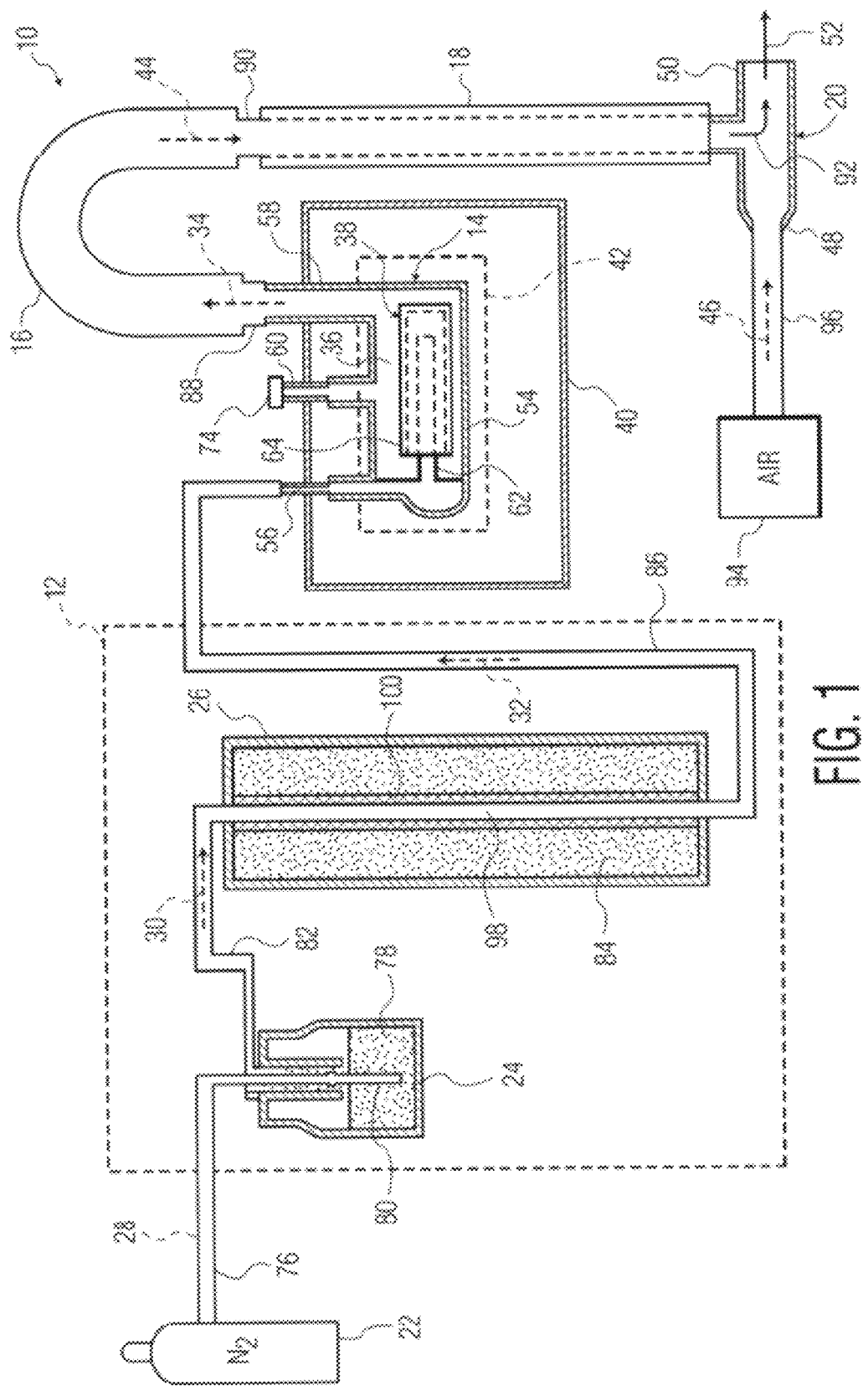
FIG. 1 is a schematic diagram of an aerosol generator for one embodiment of the present invention.

The present invention is directed generally to an aerosol generator adapted for producing a highly concentrated monodisperse aerosol composed of micron- and submicron-size particles from an aerosol material over an extended period of time, and from a relatively small volume of an aerosol material. The aerosol generator of the present invention utilizes a controlled condensation technique to produce the monodisperse aerosol. In particular, the aerosol generator of the present invention utilizes a vaporization-condensation process including, for example, heterogeneous condensation (HC). The technique involves vaporizing an aerosol material or a low volatility material, and allowing it to condense onto non-volatile seed particles or condensation nuclei. This results in the formation of an aerosol with a narrow size distribution. The aerosol generator can be used to produce monodisperse aerosols from a variety of low volatility liquid and solid materials. The aerosol generator of the present invention is configured to produce aerosols over a wide range of particles of up to 5 micrometers in diameter.

Generally, the aerosol generator of the present invention includes a saturator for forming a vapor from a low volatility material or aerosol material, and a condenser for cooling the vapor of the aerosol material to produce the monodisperse aerosol. In the present invention, a high vaporization rate is achieved with small volumes of the aerosol material through the use of a custom designed saturator. This has been proven to be a highly efficient approach for producing aerosols in the 1 to 5 micrometer size range with high output mass concentrations. Stable operation can be achieved for extended periods of time such as, for example, sixty minutes with loading volumes as low as 200 μL. The present invention provides a suitable applicability for testing of chemical agents when it is desirable to maintain quantities of test materials at a minimum.

The saturator of the present invention is designed to substantially enhance the efficiency and effective use of the aerosol material, thereby greatly reducing the loading volumes of the aerosol material and avoiding the limitations associated with prior art devices. Optionally, the aerosol generator of the present invention can further include a source of non-volatile sub-micron condensation nuclei, whereby the condenser cools the vapor of the aerosol material in the presence of the non-volatile sub-micron condensation nuclei to produce the monodisperse aerosol. The aerosol generator of the present invention is cost effective and relatively simple to make and implement.

In one embodiment of the present invention, an aerosol generator includes a saturator having an enclosure for passing a gas therethrough, and a porous substrate adapted for retaining a non-vaporized form of an aerosol material, wherein the porous substrate is further adapted to release a vaporized form of the aerosol material for introduction into the gas within the enclosure, and a condenser adapted for receiving the gas containing the vapor from the saturator to produce an aerosol containing the aerosol material.

The term "aerosol", as used herein, is a relatively stable suspension of fine solid or liquid particles in a gas such as, for example, air.

The term "monodisperse", as used herein, refers to a property of an aerosol, whereby each of the individual aerosol particles exhibits the same or substantially the same size, shape and mass characteristics within a geometric standard deviation of less than 1.15.

The term "aerosol material", as used herein, refers to any liquid or solid material having relatively low volatility at standard temperature and pressure, which is vaporized and then condensed to produce an aerosol.

The term "porous substrate", as used herein, refers to any refractory material having sufficient porosity or wicking capacity to receive and retain an amount of a low volatility material or aerosol material for subsequent vaporization, and maintaining a relatively high surface area to volume ratio with respect to a gas stream flowing in contact therewith. Preferably, the porous substrate is composed of a ceramic, including but not limited to, alumina such as, for example, fused alumina.

Referring to FIG. 1, there is shown an aerosol generator identified generally by reference numeral 10 in accordance with one embodiment of the present invention. The aerosol generator 10 is adapted to produce an aerosol through the process of vaporization-condensation, preferably heterogeneous condensation (HC). Although the present invention is described in context of a heterogeneous condensation-based system, it will be understood that the present invention can be readily adapted to produce an aerosol via the process of homogenous condensation, as one skilled in the art will recognize.

In the present embodiment, the aerosol generator 10 is configured to produce high-concentration monodisperse aerosols, while maintaining or extending the period of time of aerosol production from a relatively small volume of the aerosol material. In this manner, the aerosol generator 10 allows the user to work with smaller quantities of aerosol material that would otherwise not be possible with prior art devices.

In the present embodiment, the aerosol generator 10 includes a condensation nuclei source 12 adapted for producing condensation nuclei or seed particles, a saturator 14 adapted for holding a quantity of an aerosol material or low volatility material and producing a vapor thereof, a reheater 16 adapted for heating a gas flowing therethrough, a condensation chimney or condenser 18 adapted for cooling a gas flowing therethrough, and an aerosol dilutor 20. The condensation nuclei source 12 further includes a carrier gas source 22 for supplying an inert carrier gas such as nitrogen gas ($N_2$), an atomizer 24 (e.g., Collison atomizer), and a desiccant dryer 26.

A carrier gas 28, preferably an inert gas such as nitrogen gas, is used in the aerosol generator 10 to prevent or minimize chemical reactions with the aerosol material used. As described above, the carrier gas 28 is supplied from the carrier gas source 22 into the aerosol generator 10 via a conduit 76 to the atomizer 24. The atomizer 24 contains a salt solution 78 (e.g., a very dilute sodium chloride (NaCl) solution). As the carrier gas 28 passes therethrough, the atomizer 24 sprays the salt solution 78 from a nozzle 80 forming very tiny droplets (about 1 μm to 3 μm particle sizes) to yield a droplet-laden gas stream 30. The gas stream 30 is conveyed to the desiccant dryer 26 via a conduit 82.

The desiccant dryer 26 contains a desiccant substance or drying agent 84 (e.g., calcium oxide or silica gel) that removes water from the droplets in the gas stream 20. The gas stream 30 passes through an open channel 98 lined with a screen or mesh 100 within the desiccant dryer 26. Any moisture or water vapor diffuses through the screen 100 and absorbed by the drying agent 84 as the aerosol passes through the desiccant dryer 26. The drying process produces small crystals with sizes of from about 10 nm to 100 nm, depending on the original concentration of the salt solution 78, to yield a condensation nuclei gas stream 32.

The condensation nuclei gas stream 32 is then conveyed via a conduit 86 to the saturator 14 housed within a heating device 40. The saturator 14 includes an enclosure 36 through which the condensation nuclei stream 32 pass, and a porous substrate 38 disposed within the enclosure 36 in contact with the passing gas stream 32. The porous substrate 38 is adapted for retaining a non-vaporized form of an aerosol material, which upon heating releases a vaporized form of the aerosol material. The porous substrate 38 is configured to provide a high surface area for evaporation. The high surface area allows the operating temperature to be reduced while maintaining the rate of vaporization. The lower operating temperature also beneficially minimizes undesirable thermal degradation of the aerosol material. The saturator 14 produces a condensation nuclei-vapor gas stream 34, which is saturated with the vapor of the aerosol material. Depending on the temperature and vapor pressure, a precise saturation concentration of the vapor can be achieved in the gas stream 34.

The heating device 40 is configured to heat the porous substrate 38 and the aerosol material retained within the saturator 14. The heating device 40 preferably heats the porous substrate 38 to a temperature of from about 50° C. to 200° C. The heating device 40 can selected, for example, from a convection oven, an electrically resistive heating element or a heat bath. Preferably, the heating device 40 includes an electrically resistive heater 42, which is positioned proximate to the enclosure 36 and the porous substrate 38. In the present embodiment of the invention, the heater 42 includes an aluminum heater block in the form of a half-cylinder that partially envelops the saturator 14 without physical contact therebetween.

The carrier gas-condensation nuclei-vapor stream 34 exiting the saturator 14 is conveyed into the inlet 88 of the reheater 16. The reheater 16 includes a series of resistive heating elements (not shown) to supply heat to the gas stream 34. The gas stream 34 is heated to a temperature above the temperature of the oven 40 to yield a vapor saturated gas stream 44. This ensures that no condensation takes place upstream of the condenser 18 and that the condensation nuclei are free of any volatile materials such as residual water. This also ensures that any prematurely formed condensation is re-evaporated and does not adversely affect the formation of the aerosol. Preferably, the temperature in the reheater 16 is at least 50° C. higher, and more preferably from about 50° C. to 100° C. higher than the temperature in the saturator 14.

The heated vapor saturated gas stream 44 exits through the outlet 90 of the reheater 16 and into the condenser 18 for cooling. The condenser 18 can be air-cooled or water-cooled. The condenser 18 cools the gas stream 44 as the vapor of the aerosol material and the nuclei moves therethrough. The condenser 18 directs the flow of the gas stream 44 in a downwardly direction to promote a smooth laminar flow preventing or at least substantially minimizing the formation of eddies or turbulence. The laminar flow facilitates a uniform particle growth process.

The resulting supersaturation of the vapor of the aerosol material in the gas stream 44 causes the vapor to condense onto the condensation nuclei to yield an aerosol 92. The aerosol 92 is subsequently passed through the dilutor 20 which may optionally add a dilution gas 46 supplied by an air source 94 via a conduit 96. The dilutor 20 is adapted to greatly minimize particle aggregation or coagulation, thereby stabilizing the resulting aerosol particle size. The dilution gas 46 passes through an inlet 48 of the dilutor 20 for mixing with the aerosol 92. The resulting mixture exits an outlet 50 of the dilutor 20 to yield a sample 52 of the aerosol 92 at a desired concentration.

Figure 2:
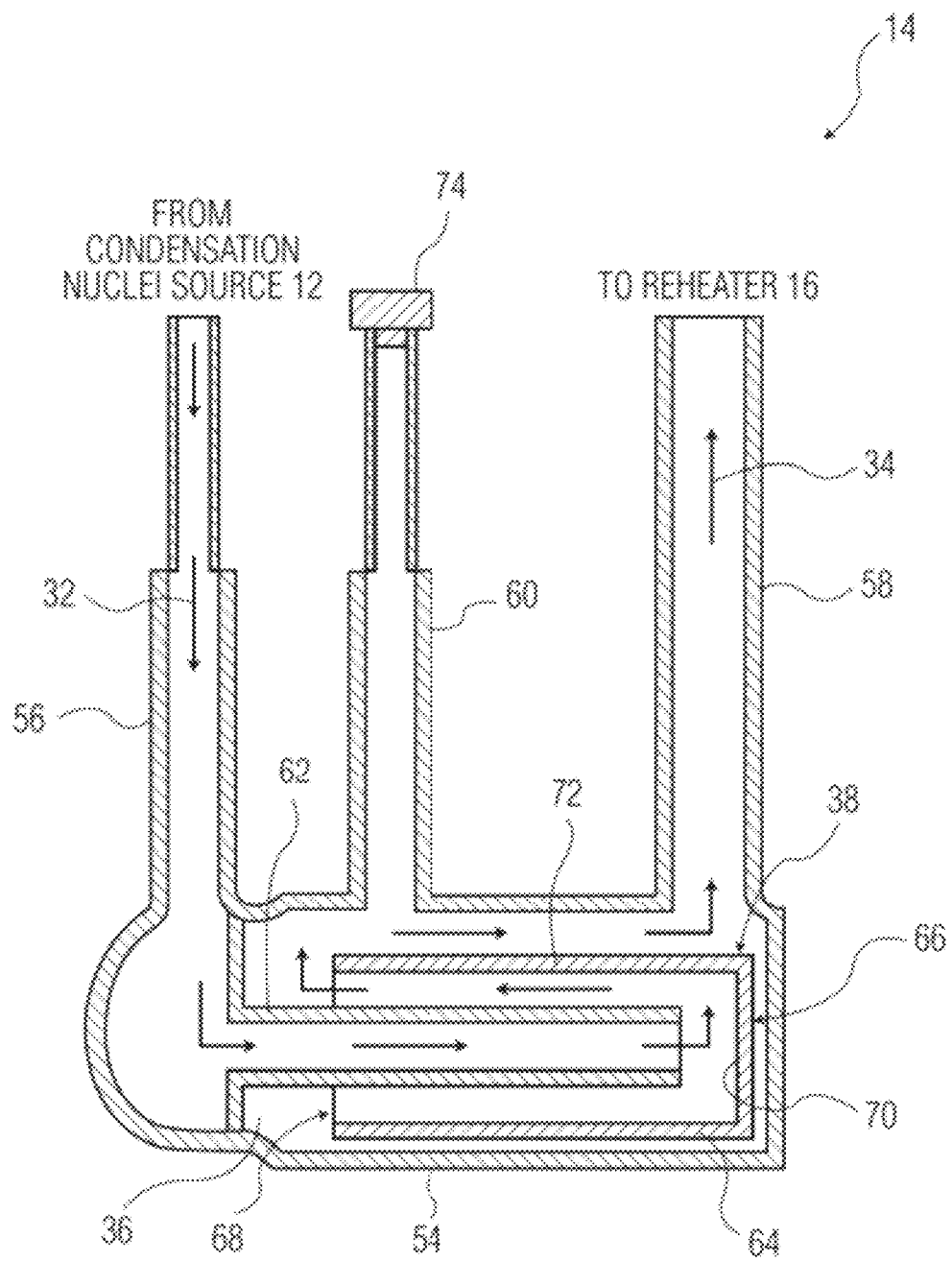
FIG. 2 is a cross-sectional view of a saturator of the aerosol generator along its longitudinal axis for one embodiment of the present invention.

Referring to FIG. 2, the saturator 14 includes a vessel 54 defining the enclosure 36 in which the porous substrate 38 is disposed, an inlet port 56, an outlet port 58 and an aerosol material loading port 60. In the present embodiment, the porous substrate 38 is a hollow ceramic thimble or tubular body 64 having a closed end 66, an open end 68, and interior and exterior surfaces 70 and 72, respectively. In the present embodiment of the invention, the ceramic thimble 64 is composed of fused alumina having an aluminum oxide ($Al_2O_3$) content of less than 90%. It will be understood that the composition of the ceramic thimble 64 is not limited to this embodiment, and may encompass any suitable ceramic or ceramic-like material as known to one of ordinary skill in the art.

The loading port 60 of the saturator 14 provides direct fluid communication with the thimble 64 in the enclosure 36 and enables the operator to load the aerosol material onto the thimble 64 via direct injection. The amount of the aerosol material can vary from about 100 μL to 1000 μL. With the ceramic thimble 64 loaded with the aerosol material, a closure cap or stopper 74 is replaced to cover the opening of the loading port 60.

Note that the porous substrate 38 can be composed of any suitable porous refractory material and/or configured to have any suitable shape or configuration suitable for facilitating the vaporization of the aerosol material. Alternatively, the porous substrate 38 may be in the form of a pellet bed, a column or any form that maximizes the surface area to volume ratio thereof provided that the configuration does not restrict the flow or passage of the condensation nuclei through the saturator 14.

The vessel 54 of the saturator 14 is configured to direct from the conduit 86 a flow of the gas stream 32 containing the carrier gas (e.g., nitrogen gas) and the condensation nuclei at a flow rate of about 1 liter per minute over the interior and exterior surfaces 70 and 72, respectively, of the porous ceramic thimble 64 in a double pass fashion. The inlet port 56 of the saturator 14 includes an internal open-ended tube or pistol 62 extending into the thimble 64 through the open end 68 thereof within the enclosure 36 of the vessel 54. During operation, the gas stream 32 entering the saturator 14 from the condensation nuclei source 12 flows into contact with the interior and exterior surfaces 70 and 72, respectively, of the thimble 64 as it passes from the inlet port 56 toward the outlet port 58, thus producing a multi-pass flow.

The wicking action of the ceramic thimble 64 allows the aerosol material to spread over the porous surfaces 70 and 72, respectively, thereby creating a large surface area for promoting vaporization. As the aerosol material vaporizes from the ceramic thimble 64, the gas stream 32 picks up the newly formed vapors and exits the vessel 54 via the outlet port 58 as the vapor saturated gas stream 34. The vaporization rate of the aerosol material from the saturator 14 is mainly a function of temperature and flow rate of carrier gas through the vessel 54 of the saturator 14.

Heating of the saturator 14 can be accomplished in any number of ways provided that the temperature surrounding the vessel 54 is controlled to within 0.5° C. or better. Examples of heating devices 40 that Applicant has tested include a 1 cubic foot convection over, a small 0.2 cubic foot custom made oven, or a constant temperature oil bath. A preferred heating device 40 is an oven having a heater 42 including a truncated cylindrical body composed of a metal having an inner diametric area for receiving and partially enclosing the saturator 14 and supplying heat to the vessel 54 housing the porous substrate 38.

The selection of the composition of the condensation nuclei is based upon factors such as compatibility with the material being aerosolized, analytical methods being applied, and the like. The presence of a very high concentration ($>10^5$ particles/cm$^3$) of condensation nuclei, however, is essential for efficient operation of the aerosol generator 10. Hence the passages through the saturator 14 must be unrestricted and sized appropriately to minimize loss of condensation nuclei via diffusional deposition in transit through the enclosure 36. The nuclei, generally less than 0.1 μm in size, can be generated by a number of different technologies ranging from compressed air atomization to a high voltage spark, provided that the method chosen produces a stable concentration of particles.

EXAMPLE

The following is a summary of recent tests in which the performance of the present aerosol generator was evaluated in terms of various operating parameters including loading volume, saturator flow rate, and heating method.

Methods:

All aerosol generator tests described herein were conducted with diethyl sebacate (DES), a low volatility colorless to yellowish liquid having a high boiling point of about 312° C. DES has been proposed as a candidate simulant for chemically hazardous operations.

The prototype aerosol generator 10 was prepared from a modified Model 3470 monodisperse aerosol generator obtained from TSI, Inc. of Minneapolis, Minn., in which the original 125 mL saturator vessel was replaced with one of two different sized multipass saturators 14 of the present invention constructed for Applicant by Glassblowers.com, Inc., of Tumerville, N.J.

Other components of the model 3470 generator system, including the saturator convection oven 40, the reheater 16, and the vapor condenser 18, were basically unchanged for the first series of tests. The first multi-pass saturator 14 of the present invention included a 25 mm OD glass tube with tubing connection at each end and was designed for working liquid volumes of 0.5 to 3 mL. The main body of the present saturator 14 contained a 19×50 mm hollow ceramic thimble 64 designed to increase the effective contact area between the challenge liquid to be vaporized and the nitrogen carrier gas. A second physically smaller saturator 14 of the present invention, containing a 13×40 mm ceramic thimble 64, was designed to work with loading volumes in the range of 0.1 mL to 1 mL.

A more transportable version of the present aerosol generator was produced by replacing the 1-cubic foot convection oven of the TSI Model 3470 with a smaller (0.15 cubic foot) custom made mini-oven 40 with no moving parts. The mini-oven 40 was sized to fit the smaller saturator 14 of the present invention with the 13×40 mm ceramic thimble 64. Performance of the mini-oven based aerosol generator 10 was tested in a more recent second series of tests.

Condensation nuclei in the form of sub-micron sodium chloride particles were formed by nebulization of a dilute aqueous saline solution (20 mg/liter) using a standard single jet Collison atomizer 24 available from BGI, Inc. of Waltham, Mass. The saline solution 78 was prepared with ultra-pure water and subsequently filtered and refrigerated to reduce impurities and to minimize bacterial growth. The atomizer 78 was operated with pressurized nitrogen at 20 psig with a resulting flow rate of about 2.4 liters per minute. Atomized droplets thus formed were passed through a desiccant drier system 26 to remove water vapor and promote complete droplet evaporation leaving a residual salt particle of sub-micron size. Nuclei production rate was initially evaluated with a Model 3022 Condensation Particle Counter available from TSI, Inc. of Minneapolis; Minn.

Aerosols produced in the present aerosol generator 10 were immediately diluted at the outlet of the air condenser 18 approximately 10-fold to form a 20 liters per minute (lpm) air stream and diverted to a multi-port sampling manifold for evaluation. The sampling manifold was interfaced to various devices designed to assess aerosol mass concentration and particle size distribution. This includes two real time aerosol monitors: the Model 8520 DustTrak™ Aerosol Monitor, and the Model 3320 Aerodynamic Particle Sizer (APS), each available from TSI, Inc. of Minneapolis, Minn., along with dual filter samplers loaded with glass fiber media (Pall Type NE, 0.3 µm). Quantification of all filter samples was accomplished by means of gravimetric analysis.

Results:

The presence of a sufficient concentration of condensation nuclei was a key factor in efficient aerosol generator operation. Initial tests, run to evaluate saline nuclei production rate from the single jet Collison atomizer 24 operated at a pressure of 20 psig, indicated a nuclei production rate of 2 to 3 million particles per minute. This is a sufficiently high seed particle production rate for maximizing the conversion of vaporized test material to usable aerosol output. Based on the saline solution concentration (20 mg/liter), and the output characteristics of the Collison atomizer 24, the median size of the condensation nuclei is estimated at 0.05 µm.

Testing of the initial prototype aerosol generator 10 using the present saturator 14 in the convection oven of the commercial generator revealed that the system was capable of producing a highly concentrated aerosol output with a well controlled and highly focused particle size distribution. Table 1 below summarizes salient results for two sizes of the present saturator 14 and various saturator flow rates at the same oven temperature.

TABLE 1

Summary of prototype aerosol generator performance

| Saturator | Load Volume (mL) | Saturator Flow (lpm) | MMAD (µm) | GSD | Operating Time (min) | Output* Conc. (mg/m³) | Generation Efficiency |
|---|---|---|---|---|---|---|---|
| 19 × 50 | 2 | 2.4 | 2.94 | 1.31 | 40 | 1240 | 50% |
| 19 × 50 | 2 | 2.4 | 2.32 | 1.37 | 40 | 1110 | 45% |
| 19 × 50 | 2 | 1.4 | 3.47 | 1.21 | 60 | 910 | 58% |
| 19 × 50 | 2 | 1.4 | 3.41 | 1.23 | 50 | 753 | 38% |
| 19 × 50 | 2 | 0.9 | 3.95 | 2.14 | 70 | 538 | 38% |
| 13 × 40 | 1 | 0.9 | 2.68 | 1.31 | 96 | 217 | 42% |
| 13 × 40 | 0.5 | 0.9 | 3.09 | 1.15 | 50 | 297 | 59% |

Oven Temperature - 136° C.; *Generator output flow = 20 lpm

With a 2 mL loading volume of the stimulant in the larger (19×50 mm) saturator 14 of the present invention, aerosol output concentrations on the order of 1 gm/m³ were easily achieved at the highest saturator flow tested (2.4 lpm). Aerosol size distributions were quasi-monodisperse with geometric standard deviations (GSD) ranging from 1.14 to 1.37. The present aerosol generator 10 was operated steadily for about 40 to 60 minutes under these conditions. Reduction of the saturator flow at the same oven temperature had the effect of reducing mass output but increased the effective operating time of the generator. Median particle size was determined to be inversely related to saturator flow, all else being the same.

Further evaluation of the prototype aerosol generator 10 with a smaller saturator 14 (13×40 mm) of the present invention was performed with intention of reducing generator loading requirements at the expense of a reduced output rate. Testing was successfully conducted with both 1 mL and 0.5 mL loading volumes with resulting stable operating times of 96 and 50 minutes respectively at comparable output concentrations of 217 mg/m³ and 297 mg/m³.

Figure 3:
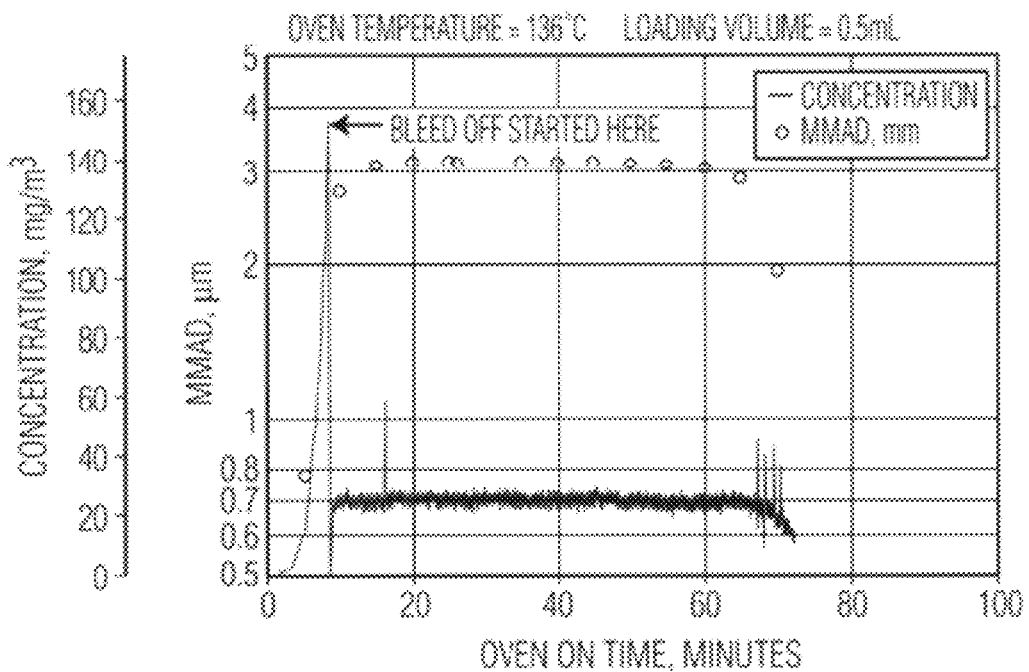
FIG. 3 is a graph showing the temporal performance characteristics of an aerosol generator of the present invention with a 0.5 mL load volume in accordance with the present invention.

FIG. 3 illustrates the temporal performance characteristics of the aerosol generator 10 with a 0.5 mL load volume. From the time that the oven 40 was turned on, aerosol concentration quickly ramped up to a level beyond the measurement range of the optical monitor at which point 90% of the aerosol was bled off as shown in FIG. 3. Particle size stabilized in about 15 minutes. For the next 50 minutes, particle size and concentration remained invariant. Finally, particle size and concentration fell off as the simulant load in the present saturator 14 is spent.

One notable feature of the prototype aerosol generator 10 was the high efficiency at which aerosol was produced as indicated in Table 1. Efficiency is defined as the ratio of the mass of aerosol generated over the stable operating period to the loading volume of material in the present saturator 14 expressed in percent. Roughly 50% of the loading volume of simulant was converted to useful test aerosol. In contrast, pneumatic atomizers typically exhibit generation efficiencies on the order of 15% or less for particles under 5 µm.

Further aerosol generator testing with the smaller footprint mini-oven 40 specifically sized for the 13×40 mm saturator 14 of the present invention was proven to be successful thus far with simulant loading volumes as low as 0.2 mL. While generator warm-up time to stable operating conditions on average increased with the mini-oven 40 in comparison to the commercial convection oven, overall performance of the generator in terms of output capability, generation efficiency and particle size stability did not change.

Figure 4:
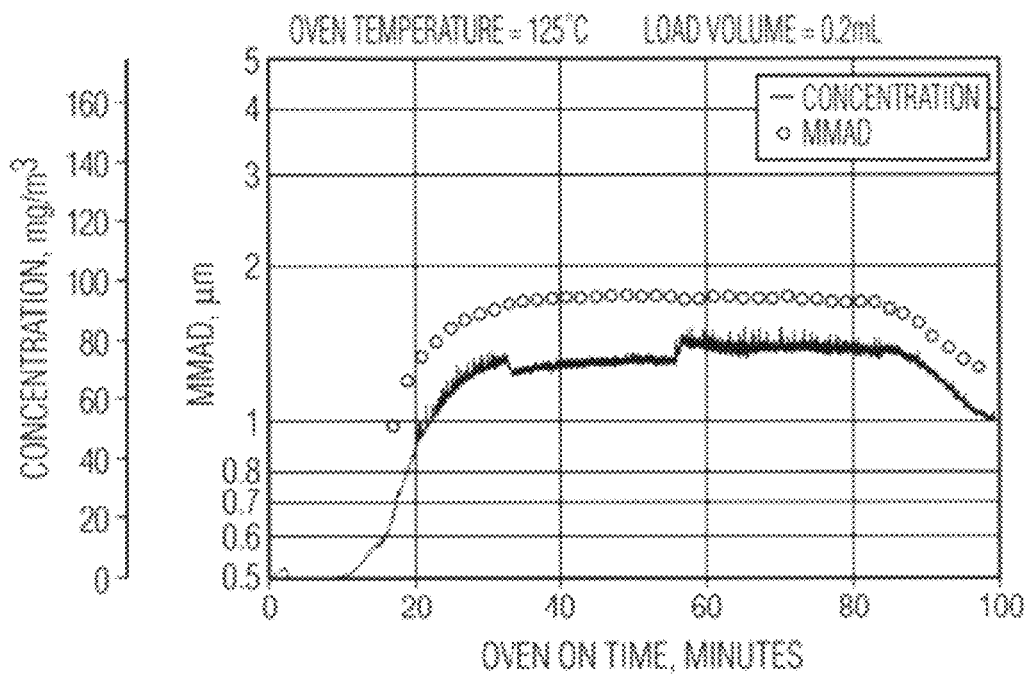
FIG. 4 is a graph showing the temporal performance characteristics of an aerosol generator of the present invention using a mini-oven with a 0.2 mL load volume in accordance with the present invention.

FIG. 4 illustrates the temporal performance characteristics of the aerosol generator 10 using the mini-oven 40 with a 0.2 mL load volume. In this case, it took the generator 10 about 30 minutes to stabilize at an aerosol particle size of 1.7 µm mass median aerodynamic diameter (MMAD). Aerosol output concentration reached steady state at about the same time. Both particle size distribution and concentration remained relatively invariant for 60 minutes. (Note that the momentary step down in aerosol concentration between 35 and 55 minutes is a sampling artifact). Saturator output and particle size dropped off sharply as vaporization of the simulant load neared completion.

In summary, the multi-pass saturator 14 of the present invention appeared to function as a vapor source for the controlled generation of test aerosols using the HC approach. Thus far, stable operation appeared to be limited to a time duration of about one hour with a single load of test material possibly placing constraints on the type of testing that can be performed. The method was proven to be a highly efficient means of dissemination with a liquid simulant, even with loading volumes as low as 200 microliters. A viable portable

CONCLUSION

The multi-pass saturator of the present invention was shown to function as a vapor source for the production of useful test aerosols of respirable size while minimizing loading requirements of material.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. An aerosol generator, comprising:
   a saturator including:
      an enclosure for passing a gas therethrough; and
      a porous substrate being adapted for retaining a non-vaporized form of an aerosol material, wherein the porous substrate is further adapted to release a vaporized form of the aerosol material for introduction into the gas within the enclosure; and
   a condenser adapted for receiving the gas containing the vapor from the saturator to produce an aerosol containing the aerosol material.

2. The aerosol generator of claim 1, further comprising a condensation nuclei source for supplying condensation nuclei to the gas passing through the enclosure of the saturator, wherein the vapor of the aerosol material condenses onto the condensation nuclei within the condenser to produce the aerosol.

3. The aerosol generator of claim 1, further comprising a reheater disposed between the saturator and the condenser, said reheater being adapted for heating the gas containing the vapor of the aerosol material to a higher temperature.

4. The aerosol generator of claim 1, wherein the condenser is adapted for passing the gas containing the vapor of the aerosol material in a downward laminar flow.

5. The aerosol generator of claim 1, further comprising a dilutor for supplying a dilution gas to the generated aerosol.

6. The aerosol generator of claim 1, wherein the porous substrate is a ceramic.

7. The aerosol generator of claim 1, wherein the enclosure of the saturator comprises a vessel having an inlet, an outlet, and an internal cavity defined therebetween for holding said porous substrate.

8. The aerosol generator of claim 7, wherein the vessel further comprises a loading port in communication with the porous substrate, for receiving the aerosol material.

9. The aerosol generator of claim 7, wherein:
   the porous substrate includes a tubular body having a closed end, an open end, and interior and exterior surfaces; and
   the inlet includes a tube extending into the porous substrate through the open end thereof, wherein the gas comes into contact with the interior and exterior surfaces of the porous substrate as it passes from the inlet to the outlet of the vessel.

10. The aerosol generator of claim 1, further comprising a heat source operatively associated with the porous substrate for heating the aerosol material.

11. The aerosol generator of claim 10, wherein the heat source is selected from the group consisting of a convection oven, a resistive heating element and a heat bath.

12. The aerosol generator of claim 2, wherein the condensation nuclei source comprises:
   a gas supply;
   to an atomizer for producing a condensation nuclei precursor in the presence of the gas; and
   a desiccant dryer.

13. An aerosol generator, comprising:
   a condensation nuclei source for supplying condensation nuclei to a gas;
   a saturator including:
      an enclosure for passing the gas containing the condensation nuclei therethrough from the condensation nuclei source; and
      a porous substrate being adapted for retaining a non-vaporized form of an aerosol material, wherein the porous substrate is further adapted to release a vaporized form of the aerosol material for introduction into the gas containing the condensation nuclei within the enclosure; and
   a condenser adapted for receiving the gas containing the vapor and condensation nuclei from the saturator, wherein the vapor of the aerosol material condenses onto the condensation nuclei within the condenser to produce an aerosol containing the aerosol material.

14. The aerosol generator of claim 13, wherein the enclosure of the saturator comprises a vessel having an inlet, an outlet, and an internal cavity defined therebetween for holding said porous substrate.

15. The aerosol generator of claim 13, wherein:
   the porous substrate includes a tubular body having a closed end, an open end, and interior and exterior surfaces; and
   the inlet includes a tube extending into the porous substrate through the open end thereof, wherein the gas comes into contact with the interior and exterior surfaces of the porous substrate as it passes from the inlet to the outlet of the vessel.

16. A saturator for an aerosol generator, comprising:
   an enclosure for passing a gas containing condensation nuclei therethrough from a condensation nuclei source; and
   a porous substrate being adapted for retaining a non-vaporized form of an aerosol material, wherein the porous substrate is further adapted to release a vaporized form of the aerosol material resulting in the formation of a vapor for introduction into the gas passing through the enclosure.

17. The saturator of claim 16, wherein the porous substrate is a ceramic.

18. The saturator of claim 16, wherein the enclosure of the saturator comprises a vessel having an inlet, an outlet, and an internal cavity defined therebetween for holding said porous substrate.

19. The saturator of claim 18, wherein the vessel further comprises a loading port in communication with the porous substrate, for receiving the aerosol material.

20. The saturator of claim 18, wherein:
   the porous substrate includes a tubular body having a closed end, an open end, and interior and exterior surfaces; and
   the inlet includes a tube extending into the porous substrate through the open end thereof, wherein the gas comes into contact with the interior and exterior surfaces of the porous substrate as it passes from the inlet to the outlet of the vessel.

* * * * *